(12) United States Patent
Tomasulo et al.

(10) Patent No.: US 8,304,537 B2
(45) Date of Patent: Nov. 6, 2012

(54) USE OF OXAZINE COMPOUNDS FOR MAKING CHROMOGENIC MATERIALS

(75) Inventors: Massimiliano Tomasulo, Miami, FL (US); Francisco M. Raymo, Coral Gables, FL (US)

(73) Assignee: The University of Miami, Miami, FL (US)

( * ) Notice: Subject to any disclaimer, the term of this patent is extended or adjusted under 35 U.S.C. 154(b) by 204 days.

(21) Appl. No.: 12/733,887

(22) PCT Filed: Oct. 17, 2008

(86) PCT No.: PCT/US2008/011909
§ 371 (c)(1),
(2), (4) Date: Mar. 25, 2010

(87) PCT Pub. No.: WO2009/051820
PCT Pub. Date: Apr. 23, 2009

(65) Prior Publication Data
US 2010/0249403 A1    Sep. 30, 2010

Related U.S. Application Data

(60) Provisional application No. 60/960,854, filed on Oct. 17, 2007.

(51) Int. Cl.
*C07D 265/12* (2006.01)
*G02B 5/23* (2006.01)
*C07D 265/00* (2006.01)

(52) U.S. Cl. .......... 544/89; 252/582; 252/586; 252/600; 359/321; 369/94; 436/164; 436/172; 544/71; 548/509

(58) Field of Classification Search ................. 252/586, 252/582, 600; 544/89, 71; 548/509; 436/109, 436/164, 172; 422/50; 359/321; 369/94
See application file for complete search history.

(56) References Cited

U.S. PATENT DOCUMENTS
5,017,698 A    5/1991    Machida et al.
(Continued)

FOREIGN PATENT DOCUMENTS
WO    2007/028080    3/2007

OTHER PUBLICATIONS

Massimiliano Tomasulo, Salvatore Sortino, Andrew J. P. White, and Francisco M. Raymo, Fast and Stable Photochromic Oxazines, J. Org. Chem. 2005, 70, 8180-8189, © 2005 American Chemical Society.*

(Continued)

*Primary Examiner* — Bijan Ahvazi
(74) *Attorney, Agent, or Firm* — Nixon & Vanderhye P.C.

(57) ABSTRACT

Heterocyclic compounds incorporating a [1,3]oxazine ring may be used to make chromogenic materials. These molecules switch from a colorless state to a colored form upon addition of either acid or base. In both instances, the [1,3] oxazine ring opens in response to the pH change forming an indolium cation, after the addition of acid, or a phenolate anion, after the addition of base. Alternatively, the switch may occur in response to a change in electrical current or potential or a change in temperature. Chromophores absorb in the visible region of the electromagnetic spectrum. Hence, their formation translates into the appearance of color. These processes are fully reversible and the original colorless state can be regenerated by switching the pH back to neutral. Thus, these halochromic compounds can be used to develop displays, filters, indicators, lenses, sensors, switches, or windows able to switch their color in response to pH changes.

26 Claims, 3 Drawing Sheets

U.S. PATENT DOCUMENTS

| | | | |
|---|---|---|---|
| 5,166,345 | A | 11/1992 | Akashi et al. |
| 6,198,655 | B1 | 3/2001 | Heath et al. |
| 7,790,068 | B2 | 9/2010 | Raymo et al. |
| 2007/0221889 | A1 | 9/2007 | Raymo et al. |
| 2008/0213625 | A1 | 9/2008 | Raymo et al. |
| 2008/0305047 | A1 | 12/2008 | Raymo et al. |
| 2009/0258429 | A1 | 10/2009 | Raymo et al. |
| 2010/0112560 | A1 | 5/2010 | Raymo et al. |
| 2010/0249403 | A1 | 9/2010 | Tomasulo et al. |
| 2011/0095243 | A1* | 4/2011 | Raymo et al. ......... 252/586 |

OTHER PUBLICATIONS

Francisco M. Raymo and Silvia Giordani, All-optical processing with molecular switches ,PNAS, Apr. 16, 2002, vol. 99, No. 8. pp. 4941-4944.*

Massimiliano Tomasulo, Ibrahim Yildiz, Sireesha L. Kaanumalle, and Francüisco M. Raymo, pH-Sensitive Ligand for Luminescent Quantum Dots, Langmuir 2006, 22, 10284-10290, © 2006 American Chemical Society.*

Massimiliano Tomasulo, Salvatore Sortino, and Francüisco M. Raymo, A Fast and Stable Photochromic Switch Based on the Opening and Closing of an Oxazine Ring, Org. Lett., vol. 7, No. 6, 2005, © 2005 American Chemical Society.*

Massimiliano Tomasulo, Salvatore Sortino, Andrew J. P. White, and Francisco M. Raymo, Chromogenic Oxazines for Cyanide Detection, J. Org. Chem. 2006, 71, 744-753, © 2006 American Chemical Society.*

Massimiliano Tomasulo, Ibrahim Yildiz, and Francüisco M. Raymo, pH-Sensitive Quantum Dots,J. Phys. Chem. B, vol. 110, No. 9, 2006, © 2006 American Chemical Society.*

Gentili et al. "Unexpected chromogenic properties of 1,3,3-trimethylspiro(indoline-2,3-[3H]naphtho [2,1-b[1,4]oxazine) in the solid phase: Photochromism, piezochromism and acidichromism" New J. Chem. 28:379-386 (2004).

Tomasulo et al. "Chromogenic oxazines for cyanide detection" J. Organic Chem. 71:744-753 (2006).

Tomasulo et al. "Colorimetric detection of cyanide with a chromogenic oxazine" Organic Lett. 7:4633-4636 (2005).

Tomasulo et al. "Amplification of the coloration efficiency of photochromic oxazines" Adv. Materials 20:832-835 (2008).

Tomasulo et al. "Fast stable photochromic switches based on the opening and closing of [1,3]oxazine rings" Asian Chem. Lett. 11:219-224 (2007).

Tomasulo et al. "A new family of photochromic compounds based on the photoinduced opening and thermal closing of [1,3]oxazine rings" J. Photochem. Photobiol. A: Chem. 200:44-49 (2008).

Tomasulo et al. "Bichromophoric photochromes based on the opening and closing of a single oxazine ring" J. Organic Chem. 73:118-126 and supporting information pp. S1-S27(2008).

Int'l Search Report for PCT/US2008/011909, three pages, mailed May 14, 2009.

Written Opinion for PCT/US2008/011909, five pages, mailed May 14, 2009.

International Preliminary Report on Patentability for PCT/US2008/011909 mailed Apr. 29, 2010.

Raymo et al. "All-optical processing with molecular switches" Proc. Natl. Acad. Sci. USA 99:4941-4944 (2002).

Raymo et al. "Fluorescence modulation with photochromic switches" J. Phys. Chem. A 109:7343-7352 (2005).

Shachkus et al. "Synthesis and study of 5a,6-dihyro-12H-indolo[2,1-b][1,3]benzoxazines" Chemistry of Heterocyclic Compounds 25:562-565; English translation of Khimiya Geterotsiklicheskikh Soedinenii 5:672-676 (1989).

Shachkus et al. "Synthesis of [1,3] benzoxazino[2,3-k]- and [2,4] benzodiazepine[3,2-k]-carbazole derivatives" Chemistry of Heterocyclic Compounds 35:729-732; English translation of Khimiya Geterotsiklicheskikh Soedinenii 6:818-821 (1999).

Tomasulo et al. "Fast and stable photochromic oxazines" J. Org. Chem. 70:8180-8189 (2005).

Tomasulo et al. "A fast and stable photochromic switch based on the opening and closing of an oxazine ring" Org. Lett. 7:1109-1112 (2005).

* cited by examiner

| | −R⁴ | −R⁵ | −R¹ | λ nm (CF₃CO₂H eq.) | λ nm (Bu₄NOH eq.) |
|---|---|---|---|---|---|
| I | −Me | −NO₂ | −H | 318 (10) | 432 (1) |
| II | −Ph | −NO₂ | −H | 308 (10) | 428 (100) |
| III | −Me | −N=N−C₆H₄−NO₂ | −H | 380 (40) | 579 (1) |
| IV | −Ph | −N=N−C₆H₄−NO₂ | −H | 376 (40) | 574 (100) |
| V | −biphenyl | −NO₂ | −H | 313 (40) | 428 (10) |
| VI | −CH=CH−Ph | −NO₂ | −H | 388 (4) | 431 (10) |
| VII | −CH=CH−biphenyl | −NO₂ | −H | 421 (90) | 431 (90) |
| VIII | −CH=CH−C₆H₄−CH=CH−Ph | −NO₂ | −H | 460 (80) | 431 (1) |
| IX | −Me | −NO₂ | −CH=CH−C₆H₄−CH=CH−Ph | 374 (90) | 405 (10) |
| X | −Ph | −NO₂ | −CH=CH−C₆H₄−CH=CH−Ph | 370 (260) | 386 (120) |

USE OF OXAZINE COMPOUNDS FOR MAKING CHROMOGENIC MATERIALS

CROSS-REFERENCE TO RELATED APPLICATION

This is a U.S national-stage application of Int'l Appln. No. PCT/US2008/011909 under 35 U.S.C. 371, filed Oct. 17, 2008; which claims the benefit of provisional Appl. No. 60/960,854, filed Oct. 17, 2007; the entire contents of which are hereby incorporated by reference.

FEDERALLY-SPONSORED RESEARCH OR DEVELOPMENT

The U.S. Government has certain rights in this invention as provided for by the terms of CHE-0237578 awarded by the National Science Foundation.

FIELD OF THE INVENTION

The invention relates to compounds that can be used to make materials (e.g., displays, filters, indicators, lenses, sensors, switches, or windows) able to switch their color in response at least to changes in light and pH.

BACKGROUND OF THE INVENTION

Organic molecules can be designed to alter reversibly their ability to absorb electromagnetic radiation in response to electricity (electrochromism), heat (thermochromism), light (photochromism), and pH (halochromism). Such energy-induced transformations can be used to switch the color of liquid, gel-sol, or solid samples under the influence of external stimulation. As a result, electrochromic, thermochromic, photochromic, and halochromic molecules can be exploited to design stimuli responsive materials for a diversity of applications. For example, displays, filters, indicators, lenses, sensors, switches, and windows may be developed relying on these functional compounds. In addition to such chromogenic materials, post-application color-changing films (e.g., solid) or coatings (e.g., liquid or gel-sol) can be designed around the functional molecules. For example, appropriate formulations of these functional molecules may be applied on the surface of a solid substrate as a film, gel-sol, or coating, and then the color of the chromogenic material may be controlled reversibly with electricity, heat, light, or pH. On the basis of these considerations, our heterocyclic compounds with halochromic response may be used to make chromogenic materials. In principle, these molecules can be the basic building blocks for the development of pH-sensitive and chromogenic coatings.

SUMMARY OF THE INVENTION

We have invented a family of heterocyclic compounds. Their basic molecular skeleton fuses the bond joining positions 1 and 2 of an indoline fragment to the bond joining positions 2 and 3 of a benzooxazine fragment. In one embodiment of the invention, the compound has Formula I:

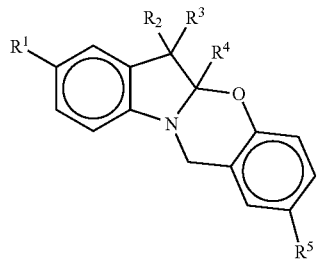

Formula I

The addition of acid to the colorless species 1a opens the [1,3]oxazine ring with the formation of the colored state 1c (FIG. 1). This compound has an indolium cation with an extended conjugate system able to absorb in the visible or ultraviolet (UV) region of the electromagnetic spectrum. The substituents $R^1$ and $R^4$ can be selected to regulate the absorption wavelength of this chromophore and, as a result the color of 1c. Addition of base to the colorless species 1a also opens the [1,3]oxazine ring with the formation of the colored state 1d (FIG. 1). This compound has a phenolate anion able to absorb in the visible or UV region of the electromagnetic spectrum. The substituent $R^5$ can be selected to regulate the absorption wavelength of this chromophore and, as a result, the color of 1d. Both processes are fully reversible and the original and colorless state 1a can be regenerated by adjusting the pH back to neutral. The two substituents $R^2$ and $R^3$ can be selected to regulate the coloration and decoloration rates.

One or more of the compound's optical properties may be measured: e.g., peak wavelength where absorbance is maximum; shift in that wavelength in response to at least pH, electrical, or thermal stimulus; intensity of absorbance at a predefined wavelength such as the peak; or a ratio of intensities at peak wavelengths before and after stimulation. Measurement includes simple visual observation of the optical material and determination of numerical parameter(s) using an optical instrument (e.g., spectrometer, monochromator, photometer).

The halochromic compounds can be used to make chromogenic materials and to develop displays; filters, indicators, lenses, sensors, switches, and windows able to switch their color in response to pH changes. Alternatively, they may have electrochromic or thermochromic properties.

BRIEF DESCRIPTION OF THE DRAWINGS

FIG. 2 is a schematic of the synthesis of the halochromic oxazine 3a from the known precursor 2a.

DESCRIPTION OF SPECIFIC EMBODIMENTS

Figure 1:
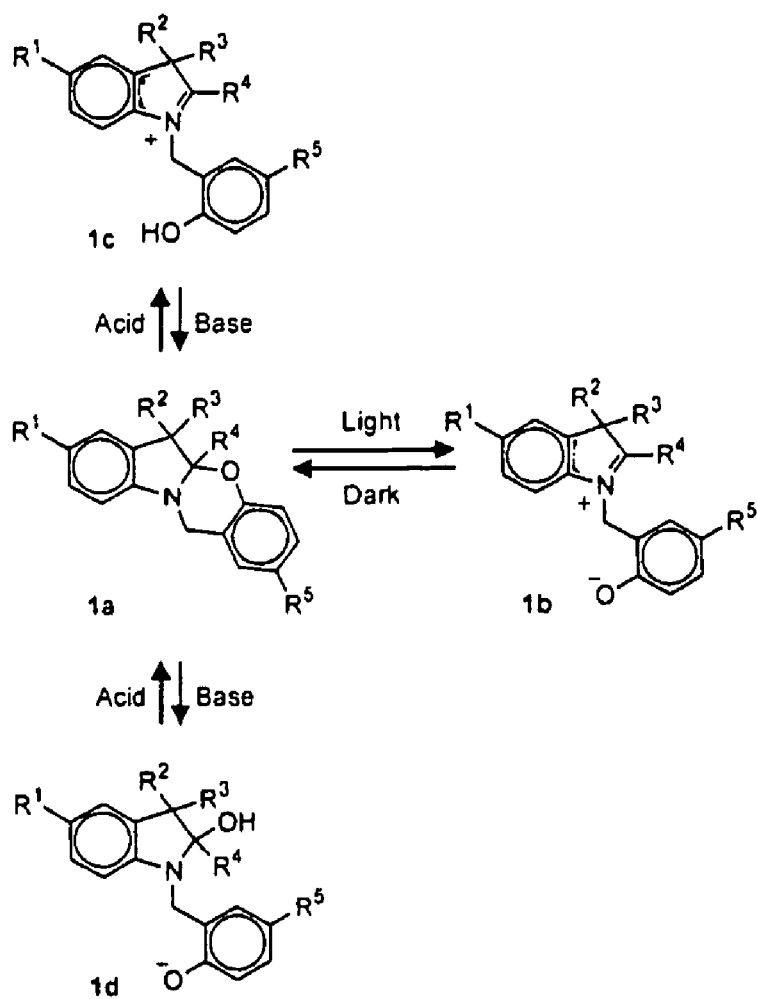
FIG. 1 is a schematic of halochromic and photochromic compounds, and their pH or light induced transformations.

We have developed a family of heterocyclic compounds of Formula I which may be used to make chromogenic materials. Cleavage of a [C—O] bond in the [1,3]oxazine ring produces a phenolate derivative, which preferably absorbs visible light. Substituents $R^1$, $R^4$ and $R^5$ can be selected to determine the absorbance wavelength of the chromophore. Selection of $R^2$ and $R^3$ (e.g., methyl substituents) can affect the rates of isomerization and/or re-isomerization. In particular, colorless and colored states may be switched by changing pH from a resting level, and then restoring the pH to allow thermal reisomerization. A hemiaminal form may be trapped with a nucleophile that competes with the ring-closing reaction to form the hemiaminal.

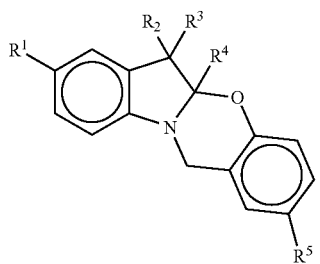

Formula I

In an embodiment of the invention, $R^1$, $R^2$, $R^3$ and $R^4$ be independently chosen from azo (e.g., 4-nitrophenyldiazene), alkyl, amide, amine, aryl, halide, carboxylic acid, cyano, ester, and nitro groups or simply a hydrogen atom. Alternatively, instead of attachment at the para position relative to the ring nitrogen atom, $R^1$ may be attached to any position on the phenylene ring of the indole fragment. $R^5$ may be an azo (e.g., 4-nitrophenyldiazene), aryl, halide, carboxylic acid, cyano, ester, or nitro group. As an alternative to attachment at the para position relative to the ring oxygen atom, $R^5$ may be attached to any position on the phenoxy ring of the benzoxazine fragment.

In other embodiments of the invention, $R^1$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl (e.g., halide, hydroxyl), C5-C6 heterocycle, or substituted (e.g., halide, hydroxyl) C5-C6 heterocycle. $R^1$ may be positioned at any position on the phenylene ring of the indole fragment, but the position opposite the attachment point of the nitrogen atom is preferred. $R^2$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl, C5-C6 heterocycle (e.g., ring-substituted oxygen or sulfur), or substituted (e.g., halide, hydroxyl) C5-C6 heterocycle. $R^3$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl, C5-C6 heterocycle (e.g., ring-substituted oxygen or sulfur), or substituted (e.g., halide, hydroxyl) C5-C6 heterocycle. $R^4$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl, C5-C6 heterocycle (e.g., ring-substituted oxygen or sulfur), substituted (e.g., halide, hydroxyl) C5-C6 heterocycle, or fused ring systems (e.g., biphenyl or diarylethene with an optional linker such as vinylidene). $R^5$ may be a nitrogen-containing group (e.g., nitroso, nitro, azo dyes) or any other electron withdrawing substituent (e.g., cyano, halides). $R^5$ may be positioned at any position on the phenoxy ring of the benzooxazine fragment, but the position opposite the attachment point of the oxygen atom is preferred. The relative orientation of the fused, substantially planar heterocycles constrains the dihedral angle between the axis of the $2p_z$ orbital on the indoline nitrogen atom and that of the adjacent $\sigma_{C-O}$ orbital. Bulky substituents at $R^2$, $R^3$, and $R^4$ near the dihedral angle are avoided.

Depending on the choice of substituents in the compound, the switch results in the maximum absorbance wavelength to shift by a positive or negative difference of at least 50 nm, at least 100 nm, at least 150 nm, at least 200 nm, at least 250 nm, or at least 300 nm. Most compounds in a composition may switch between isomeric states within 5 ns or less, 10 ns or less, 50 ns or less, or 250 ns or less. Compounds may remain able to switch and then revert over greater than 1000 cycles, greater than 3000 cycles, or greater than 5000 cycles.

The compound may be incorporated in silica, a liquid crystal, or a polymeric material or in one or more sheets of such material as a laminate. The material may be a flexible or rigid solid, preferably it is transparent or translucent. Alternatively, the compound, may be dissolved in a liquid (e.g., solution or gel-sol) and then incorporated in a solid material (e.g., applied in a thin film, cast or molded as a sheet, segregated in beads or laminated structures). The material may be amorphous (e.g., glass) or crystalline (e.g., quartz). Examples of polymeric materials include polycarbonate, polymethylmethacrylate, and polystyrene.

If incorporated in solid material (e.g., coated thereon or encapsulated therein), the material is preferably at least opaque to the wavelength of light that induces switching in the compound and does not attenuate the intensity of light such that switching is not efficient. In particular, the compounds may be dissolved in an organic solvent and its function is not oxygen sensitive.

The [1,3]oxazine ring of these compounds opens in response to optical stimulation to generate the corresponding isomer 1b (FIG. 1) with concomitant formation of a phenolate chromophore and the appearance of color. This process is thermally reversible and the original state is spontaneously regenerated when the optical stimulation is removed. Indeed, photochromic properties of some of these compounds were disclosed in US 2007/0221889 A1, which is incorporated by reference in its entirety.

Figure 2:
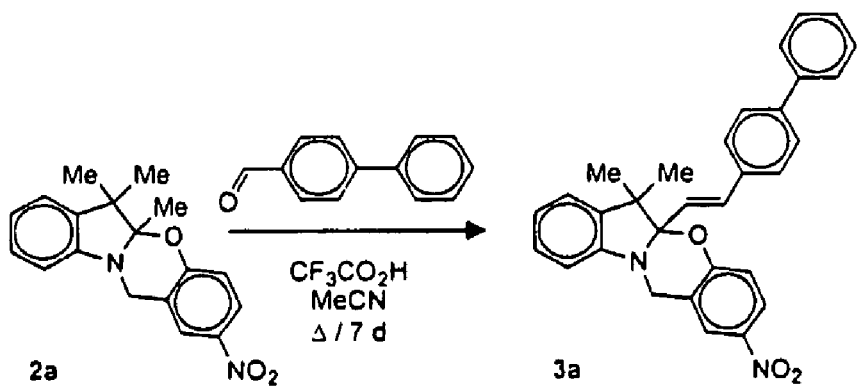
Figure 3:
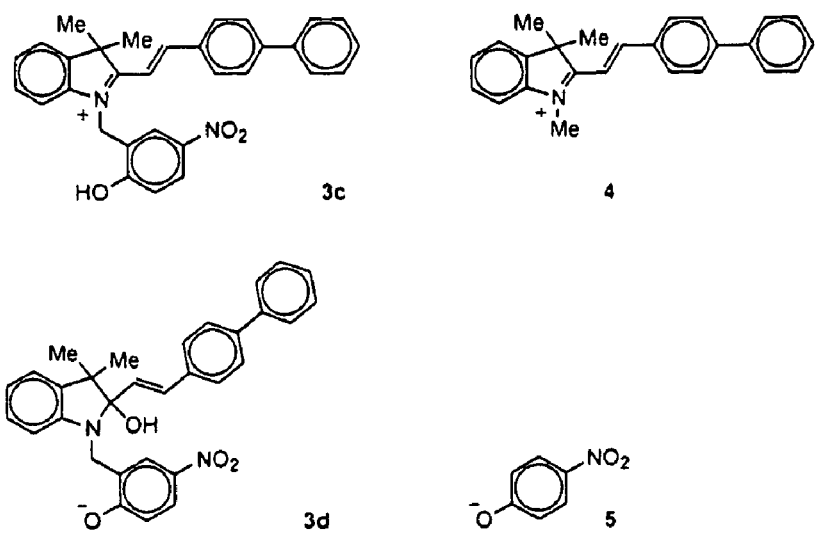
FIG. 3 illustrates colored species 3c and 3d and their model chromophores 4 and 5.

The class of photochromic oxazine compounds disclosed herein are also halochromic, and may have electrochromic and thermochromic properties as well. Specifically, their [1,3]oxazine ring opens after the addition of either acid or base to generate 1c or 1d (FIG. 1), respectively. Both processes are fully reversible and the original state can be regenerated simply by switching the pH back to neutral. The compounds 1c has an indolium cation with an extended conjugated system. The compound 1d has a phenolate anion. Both chromophores can be designed to absorb in the visible region by carefully selective the nature of $R^1$, $R^4$ and $R^5$ (FIG. 1). These substituents can be regulated independently. As a result, 1c and 1d can be engineered to have either the same or different color. For example, the [1,3]oxazine 3a (FIG. 2) switches from a colorless to a colored from when treated with either acid or base because of the formation of 3c or 3d (FIG. 3), respectively. Indeed, the absorption spectrum (a in FIG. 4)

of 3a does not show any significant absorption in the visible region. Upon addition of acid, the [1,3]oxazine ring opens to form 3c, bringing the biphenylvinyl group in conjugation with the adjacent indolium cation. The resulting extended conjugated system absorbs in the visible region and, in fact, this transformation is accompanied by the appearance of an intense band centered at ca. 430 nm in the absorption spectrum (b in FIG. 4). In agreement with this interpretation, this absorption resembles the band of the model compound 4 (c in FIG. 4), which essentially incorporates the same chromophore of 3c (FIG. 3).

Figure 4:
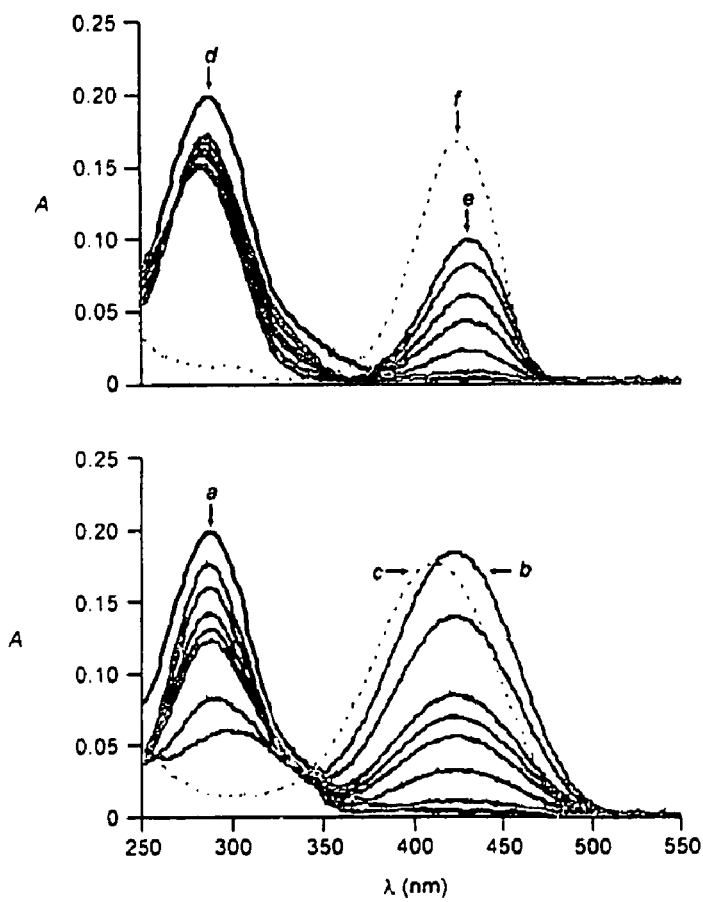
FIG. 4 shows steady-state absorption spectra (0.01 mM, MeCN, 20° C.) of 3a before (a and d) and after the addition of increasing amounts of either $CF_3CO_2H$ (0.2-10 eq., b) or $Bu_4NOH$ (40-240 eq., e), the hexafluorophosphate salt of 4 (c) and the tetrabutylammonium salt of 5 (d).

The addition of base to 3a also causes its [1,3]oxazine ring to open with the formation of 3d and the appearance of a band centered at 430 nm in the absorption spectrum (e in FIG. 4). This band resembles the one of the model compound 5 (f in FIG. 4) and is associated with the 4-nitrophenolate chromophore of 3d (FIG. 3).

Figures 5, 6:
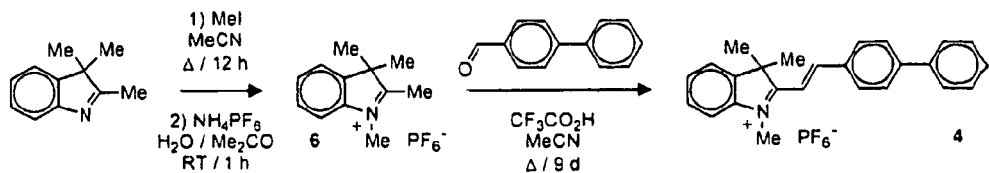
FIG. 5 is a schematic of synthesis of the hexafluorophosphate salt of the model chromophore 4.
FIG. 6 is a table of different compounds with the indicated substituents at $R^1$, $R^4$ and $R^5$. For these compounds, $R^2$ and $R^3$ are both —$CH_3$. The peak wavelength (λ nm) was measured at the indicated equivalents of $CF_3CO_2H$ acid or $Bu_4NOH$ base for each of the ten halochromic compounds.

Responsiveness to a change in pH was also shown for the compounds (Formula I with $R^2$ and $R^3$ being methyl substituents) listed in FIG. 6. For the diverse collection of $R^1$, $R^4$ and $R^5$ substituents, all ten compounds were halochromic when assayed at steady state with $CF_3CO_2H$ acid or $Bu_4NOH$ base. UV irradiation of the colorless [1,3]oxazines (1a in FIG. 1) will generate the colored zwitterions (1b in FIG. 1), which can then switch back to its original species upon storage in the dark.

In summary, the colorless state 3a switches to the colored forms 3c and 3d upon addition of acid and base, respectively. The associated changes in color can be reverted by switching the pH back to neutral. Thus, these halochromic compounds can be used to develop coatings, filters, indicators, sensors, switches, and windows able to switch their color in response to pH changes (e.g., relative concentrations of $H^+$ and $OH^-$, or acids and bases).

Materials & Methods

Chemicals were purchased commercially and used as received with the exception of MeCN, which was distilled over $CaH_2$. The [1,3]oxazine 2a was prepared according to literature procedures. The reactions were monitored by thin-layer chromatography, using aluminum sheets coated with silica (60, $F_{254}$). The melting point (mp) was determined with an Electrothermal Mel-Temp apparatus. High performance liquid chromatography (HPLC) was performed with a BDS column (dimensions=4.6×250 mm, flow rate=1.0 mL min$^{31\ 1}$, injection volume=20 μL, sample concentration=0.1 mM, solvent=MeCN) using a Varian Prostar HPLC system. The retention time (RT) and the peak asymmetry (PA) were determined at a wavelength of 278 nm. The average purity parameter (APP) was calculated for the peak heart in the wavelength range 200-800 nm. The fast atom bombardment mass spectra (FABMS) were recorded with a VG Mass Lab Trio-2 spectrometer, using 3-nitrobenzyl alcohol as matrix. The nuclear magnetic resonance (NMR) spectra were recorded with Bruker Avance 300, 400 or 500 spectrometers. The steady-state absorption spectra were recorded with a Varian Cary 100 Bio spectrometer, using quartz cells with a path length of 0.5 cm.

2-Nitro-5a-2-(4-phenylphenylene)ethylene-6,6-dimethyl-5a, 6-dihydro-12H-indolo[2,1-b][1,3]benzooxazine (3a). A solution of 2a (100 mg, 0.3 mmol), 4-biphenylcarboxaldehyde (175 mg, 1.0 mmol), and $CF_3CO_2H$ (80 μL, 0.1 mmol) in MeCN (15 mL) was heated under reflux and Ar for 7 d. After cooling down to ambient temperature, the solvent was distilled off under reduced pressure. The solid residue was dissolved in $CH_2Cl_2$ (5 mL) and the solution was diluted with hexane (50 mL). The resulting precipitate was filtered off and crystallized from PhMe (10 mL) to give 3a (60 mg, 40%) as an orange solid. mp=194° C.; HPLC: RT=4.1 min, PA=1.4, APP=236.7±0.3 nm; FABMS: m/z=475 [M+H]$^+$; $^1$H-NMR (500 MHz, CDCl$_3$): δ=1.27 (6H, s), 4.61 (2H, s), 6.42 (1H, d, 16 Hz), 6.62 (1H, d, 7 Hz), 6.85-6.91 (3H, m), 7.11-7.16 (2H, m), 7.36 (1H, t, 7 Hz), 7.35-7.38 (4H, m), 7.58-7.60 (4H, m), 7.99 (1H, dd, 3 and 9 Hz), 8.02 (1H, d, 3 Hz); $^{13}$C-NMR (100 MHz, CDCl$_3$): 30.1, 41.1, 50.5, 104.1, 109.2, 118.1, 120.4, 121.1, 122.7, 123.6, 124.3, 124.4, 127.4, 127.7, 127.8, 128.0, 128.1, 129.2, 134.9, 136.1, 138.6, 140.8, 141.1, 141.9, 146.8, 159.6.

1,3,3-Trimethyl-2-(4-phenylphenylene)ethylene-3H-indolium (4) hexafluorophosphate. A solution 6 (50 mg, 0.2 mmol), 4-biphenylcarboxaldehyde (41 mg, 0.2 mmol) and $CF_3CO_2H$ (24 μL, 0.03 mmol) in MeCN (20 mL) was heated under reflux and Ar for 9 d. After cooling down to ambient temperature, the solvent was distilled off under reduced pressure. The solid residue was purified by column chromatography (SiO$_2$:hexane/MeCO$_2$Et (2:1, v/v)→MeCO$_2$Et/MeOH (3:1, v/v) to afford 4 (52%, 40 mg) as a yellow solid. FABMS: m/z=338 [M−PF$_6$]$^+$; $^1$H-NMR (500 MHz, CDCl$_3$): δ=1.85 (6H, s), 4.39 (3H, s), 7.42-7.45 (1H, m), 7.50 (2H, t, 8 Hz), 7.56-7.65 (4H, m), 7.68 (2H, d, 8 Hz), 7.80 (2H, d, 8 Hz), 7.94 (1H, d, 16 Hz), 8.11 (2H, d, 8 Hz), 8.21 (1H, d, 16 Hz); $^{13}$C-NMR (75 MHz, CDCl$_3$): δ=27.1, 35.1, 52.9, 112.4, 115.0, 122.9, 127.7, 128.5, 129.5, 130.2, 130.3, 131.8, 133.6, 139.8, 141.7, 143.3, 146.9, 154.9, 182.7.

1,2,3,3-Tetramethyl-3H-indolium (6) Hexafluorophosphate. A solution of 2,3,3-trimethyl-3H-indole (200 μL, 1.3 mmol) and MeI (100 μL, 1.6 mmol) in PhMe (20 mL) was heated at 80° C. for 12 h under $N_2$. After cooling down to ambient temperature, the solvent was distilled off under reduced pressure. The residue was suspended in hexane (20 mL), sonicated for 30 min and filtered off to afford the iodide salt of 6 (84%, 0.33 g) as a purple solid. FABMS: m/z=174 [M−I]$^+$; $^1$H-NMR (300 MHz, CDCl$_3$): δ=1.69 (6H, s), 3.13 (3H, s), 4.30 (3H, s), 7.55-7.58 (2H, m), 7.59-7.62 (2H, m), 7.66-7.67 (1H, m); $^{13}$C-NMR (100 MHz, CD$_3$CN): δ=14.5, 21.9, 35.3, 54.8, 115.4, 123.7, 129.6, 130.3, 142.1. A solution of NH$_4$PF$_6$ (0.75 g, 5 mmol) in H$_2$O (5 mL) was added to a solution of the iodide salt of 6 (1.38 g, 5 mmol) in Me$_2$CO (30 mL). The mixture stirred for 1 h, concentrated to ca. 10 mL under reduced pressure and cooled down to 5° C. The resulting precipitate was filtered to give the hexafluorophosphate salt of 6 (95%, 1.40 g) as a pink solid.

In stating a numerical range, it should be understood that all values within the range are also described (e.g., one to ten also includes every integer value between one and ten as well as all intermediate ranges such as two to ten, one to five, and three to eight).

All modifications and substitutions that come within the meaning of the claims and the range of their legal equivalents are to be embraced within their scope. A claim reciting "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A method of switching reversibly optical properties of a compound or a material containing the compound by a change in electric current or potential, temperature, or pH; wherein said compound is of Formula I:

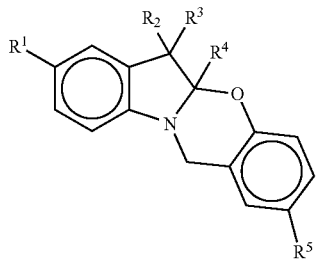

Formula I wherein (i) $R^1$, $R^2$, $R^3$ and $R^4$ are independently selected from the group consisting of hydrogen, hydroxyl, C5-C6 cycloalkyls, substituted C5-C6 cycloalkyls, C5-C6 heterocycles, substituted C5-C6 heterocycles, azo, alkyl, amide, amine, aryl, halide, carboxylic acid, cyano, ester, and nitro groups, and fused ring systems; and (ii) $R^5$ is selected from the group consisting of azo, aryl, halide, carboxylic acid, cyano, ester, and nitro groups; and other electron withdrawing substituents; said method comprising:
   (a) stimulating the compound or material by at least a change in electric current or potential, temperature, or pH; and
   (b) measuring one or more optical properties of the stimulated compound or material.

2. The method according to claim 1, wherein said switching results in reversible change from a colorless to a colored state.

3. The method according to claim 1, wherein $R^1$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

4. The method according to claim 1, wherein $R^2$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

5. The method according to claim 1, wherein $R^3$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

6. The method according to claim 1, wherein $R^2$ and $R^3$ are the same.

7. The method according to claim 1, wherein $R^4$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, substituted C5-C6 heterocycles, and fused ring systems.

8. The method according to claim 1, wherein $R^4$ is different from $R^2$ and $R^3$.

9. The method according to claim 1, wherein $R^5$ is a nitrogen-containing group or any other electron withdrawing substituent.

10. The method according to claim 1, wherein $R^5$ is 4-nitrophenyldiazene.

11. A method of switching reversibly optical properties of a compound or a material containing the compound by a change in pH, wherein switching results in reversible change from a colorless to a colored state; wherein said compound is of Formula I:

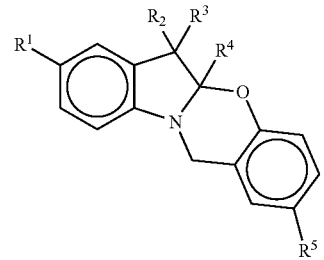

Formula I wherein (i) $R^1$, $R^2$, $R^3$ and $R^4$ are independently selected from the group consisting of hydrogen, hydroxyl, C5-C6 cycloalkyls, substituted C5-C6 cycloalkyls, C5-C6 heterocycles, substituted C5-C6 hheterocycles, azo, alkyl, amide, amine, aryl, halide, carboxylic acid, cyano, ester, and nitro groups, and fused ring systems; and (ii) $R^5$ is selected from the group consisting of azo, aryl, halide, carboxylic acid, cyano, ester, and nitro groups; and other electron withdrawing substituents; said method comprising:
   (a) stimulating the compound or material by at least a change in electic current or potential, temperature, or pH; and
   (b) measuring one or more optical properties of the stimulated compound or material;
   wherein acid induces cleavage of the [C—O] bond of the [1,3]oxazine ring to produce an indolium cation.

12. The method according to claim 11, wherein $R^1$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

13. The method according to claim 11, wherein $R^2$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

14. The method according to claim 11, wherein $R^3$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

15. The method according to claim 11, wherein $R^2$ and $R^3$ are the same.

16. The method according to claim 11, wherein $R^4$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, substituted C5-C6 heterocycles, and fused ring systems.

17. The method according to claim 11, wherein $R^4$ is different from $R^2$ and $R^3$.

18. The method according to claim 11, wherein $R^5$ is a nitrogen-containing group or any other electron withdrawing substituent.

19. A method of switching reversibly optical properties of a compound or a material containing the compound by a change in pH, wherein said switching results in reversible change from a colorless to a colored state; wherein said compound is of Formula I:

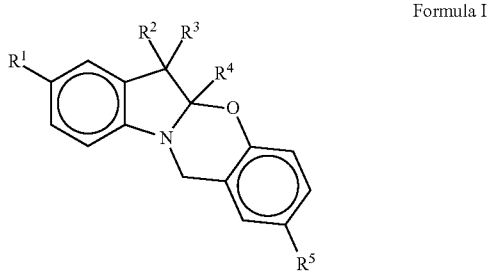

Formula I wherein (i) $R^1$, $R^2$, $R^3$ and $R^4$ are independently selected from the group consisting of hydrogen, hydroxyl, C5-C6 cycloalkyls, substituted C5-C6 cycloalkyls, C5-C6 heterocycles, substituted C5-C6 heterocycles, azo, alkyl, amide, amine, aryl, halide, carboxylic acid, cyano, ester, and nitro groups and fused ring systems; and (ii) $R^5$ is selected from the group consisting of azo, aryl, halide, carboxylic acid, cyano, ester, nitro groups; and other electron withdrawing substituents; said method comprising:
(a) stimulating the compound or material by at least a change in electric current or potential, temperature, or pH; and
(b) measuring one or more optical properties of the stimulated compound or material;
wherein base induces cleavage of the [C—O] bond of the [1,3]oxazine ring to produce phenolate anion.

20. The method according to claim 19, wherein $R^1$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

21. The method according to claim 19, wherein $R^2$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

22. The method according to claim 19, wherein $R^3$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles.

23. The method according to claim 19, wherein $R^2$ and $R^3$ are the same.

24. The method according to claim 19, wherein $R^4$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, substituted C5-C6 heterocycles, and fused ring systems.

25. The method according to claim 19, wherein $R^4$ is different from $R^2$ and $R^3$.

26. The method according to claim 19, wherein $R^5$ is a nitrogen-containing group or any other electron withdrawing substituent.

* * * * *